US008275450B2

(12) United States Patent
Winchester, Jr. et al.

(10) Patent No.: US 8,275,450 B2
(45) Date of Patent: Sep. 25, 2012

(54) MULTIPLE IMAGES, MULTIPLE EXPOSURE TIMES, OPTICAL IMAGING OF BLOOD CIRCULATION VELOCITIES

(75) Inventors: Leonard W. Winchester, Jr., Yorktown, VA (US); Nee-Yin Chou, Yorktown, VA (US)

(73) Assignee: WinTec LLC, Yorktown, VA (US)

( * ) Notice: Subject to any disclaimer, the term of this patent is extended or adjusted under 35 U.S.C. 154(b) by 521 days.

(21) Appl. No.: 12/536,017

(22) Filed: Aug. 5, 2009

(65) Prior Publication Data
US 2011/0034810 A1 Feb. 10, 2011

(51) Int. Cl.
*A61B 5/02* (2006.01)
(52) U.S. Cl. .................... 600/479; 600/473; 382/128
(58) Field of Classification Search .................. 600/301, 600/310, 317, 322, 324, 326, 328, 363, 450, 600/465, 473, 481, 504; 382/128, 130, 134, 382/164, 165
See application file for complete search history.

(56) References Cited

U.S. PATENT DOCUMENTS

| | | | | | |
|---|---|---|---|---|---|
| 4,952,050 | A | * | 8/1990 | Aizu et al. | 351/221 |
| 5,090,799 | A | * | 2/1992 | Makino et al. | 351/221 |
| 6,159,151 | A | * | 12/2000 | Bonnefous | 600/440 |
| 2002/0027649 | A1 | * | 3/2002 | Chudner | 356/39 |
| 2006/0155193 | A1 | * | 7/2006 | Leonardi et al. | 600/473 |
| 2007/0232872 | A1 | * | 10/2007 | Prough et al. | 600/316 |

OTHER PUBLICATIONS

L.W. Winchester, Jr. et al., Blood Velocity Measurements Using Laser Speckle Imaging, Sep. 1, 2004.
Nee-Yin Chou et al., Retinal Blood Velocity Measurements Using Laser Speckle Imaging, Jan. 17, 2006.
Leonard W. Winchester, et al., Measurement of Sublingual Blood Velocity as a Tool for Monitoring Sepsis, Aug. 20, 2008.
Leonard W. Winchester, et al., Measurement of Retinal Blood Velocity, Mar. 7, 2006.
Leonard W. Winchester, et al., Monitoring Free Tissue Transfer Using Laser Speckle Imaging, Feb. 22, 2006, Proc. of SPIE vol. 6078 60780G-1-8.
Shuai Yuan, et al., Determination of Optimal Exposure time for Imaging of Blood Flow Changes with LaserSpeckle Contrast Imaging, Apr. 1, 2005, Applied Optics, vol. 44, No. 10, pp. 1823-1830.
Kevin R. Forrester, et al., A Laser Speckle Imaging Technique for Measuring Tissue Perfusion, Nov. 2004, IEEE Transaction on Biomedical engineering, vol. 51, No. 11, pp. 2074-2084.
J. David Briers, et al., Laser Speckle Contrast Analysis (LASCA): A Non-scanning, Full-Field Technique for Monitoring Capillary Blood Flow, Journal of Biomedical Optics, Apr. 1997, vol. 1, No. 2, pp. 174-179.
R. Bonner, et al., Model for Laser Doppler Measurements of Blood Flow, Applied Optics, Jun. 15, 1981, vol. 20, No. 12, pp. 2097-2107.

* cited by examiner

*Primary Examiner* — James Kish
*Assistant Examiner* — Michael N Fisher

(57) ABSTRACT

A method of measuring blood velocity includes obtaining a first velocity image by illuminating a tissue surface with a light source for a first exposure time, obtaining a second velocity image by illuminating the tissue surface with the light source for a second exposure time, computing a first average intensity of a first pixel block at a first predetermined location of the first velocity image and a second average intensity of a second pixel block at a second predetermined location of the second velocity image, identifying mid-range velocities of the first and second pixel blocks, computing an optimal optical coherence parameter based on the mid-range velocity of the first pixel block and the mid-range velocity of the second pixel block, and iteratively re-computing the first velocity image and the second velocity image using the optimal optical coherence parameter.

15 Claims, 4 Drawing Sheets

RELATED ART

MULTIPLE IMAGES, MULTIPLE EXPOSURE TIMES, OPTICAL IMAGING OF BLOOD CIRCULATION VELOCITIES

BACKGROUND OF THE INVENTION

1. Field of the Invention

The present invention relates to sensing blood velocities in tissues such as, but not limited to, skin, skin flaps, transplants, breasts, retinas, and internal organs and tissue.

2. Discussion of the Related Art

The evaluation of hemodynamics is an important diagnostic subject and has been one of the most difficult challenges in medicine. In studies of skin it is important to assess blood velocities over the area of interest to determine blood perfusion and predict tissue viability. For surgical procedures involving skin flaps, a reliable method of quantitatively monitoring tissue blood velocity can provide predictive value in assessing tissue conditions during partial detachments, and before, during, and after reattachment to avoid tissue necrosis. The same is true in the transplant of tissues and organs, and before, during, and following surgery.

It is important to diagnose tissue damage due to complications of diabetes, address practicality and viability of tissue repairs and vascular densities, and detect angiogenesis in large sites being studied for possible carcinomas, for example, breast cancer. It is also important to assess blood perfusion and blood velocities in real-time and to be able to provide the information to attending medical personnel in manners that are readily perceivable and understandable. Accordingly, there is a need for assessing surgical procedures regarding reconstructive surgery involving flaps, the treatment of vascular diseases, the condition of diabetic complications, the progression of tumors, and monitoring the status of surgically implanted flaps.

Free tissue transfer is a routine surgical procedure. Complications generally occur within 48 hours of the initial surgery. Tissue necrosis sets in if poor tissue perfusion is not corrected within 12 hours of surgery. The need for early detection of vascular insufficiency in free flaps is important since the success of corrective surgery strongly depends on the time elapsed since the onset of vascular insufficiency. Between 12% and 17% of flap surgery cases require re-exploration due to post-operative vascular complications that threaten flap viability. Flap salvage rates can be as high as 50%, depending on the procedure and the elapsed time since the onset of vascular occlusion.

Flap viability can be assessed by clinical observations of flap color, tissue turgor, capillary refill, and bleeding after a pinprick. Tissue viability monitoring techniques include laser Doppler velocimetry (LDV), differential thermometry, transcutaneous oxygen measurement, plethysmography, and Doppler ultrasound. Clinical visual observation remains the standard for assessing tissue viability. Early detection of decreased blood supply to the flap can prevent wide-scale tissue necrosis and eliminate the need for additional surgical procedures.

Measurement of retinal blood velocities is an important application of the invention. The retina provides direct optical access to both the central nervous system (CNS) and afferent and efferent CNS vasculature. This unique feature has provided generations of ophthalmologists with the ability to evaluate multi-system diseases without invasive diagnostic testing using direct opthalmoscopy, indirect opthalmoscopy, and slit lamp biomicroscope examination utilizing 90 or 78 diopter lenses, and the Hruby lens. These methods, however, cannot directly and reproducibly quantify retinal blood velocity, nor do they detect preclinical alterations predictive of eventual significant morbidity. This is particularly pertinent to the insidious onset of glaucoma and macular degeneration. The trend toward preventive medicine prescribes a more sensitive technique to reliably quantify subtle changes in retinal hemodynamics.

Both incoherent and coherent optical techniques have been used to assess microcirculation. The incoherent approach includes the fluorescein dye dilution method and the blue field entoptic method for retinal blood velocity measurement, and plethysmography. The coherent approach is represented by the laser Doppler method and the dynamic laser speckle method. The former employs a focused laser beam to measure the frequency shifts of radiation scattered by a scatterer. It requires a scanning mechanism for imaging applications. Its application to turbid media requires a consideration of multiple scattering effects. The dynamic laser speckle technique has been used for both point measurements and imaging applications in cases where multiple scattering is not prominent, e.g., monitoring blood and lymph flow in microvessels and in visualizing retinal microcirculation. Taking advantage of the advanced digital photography, the Laser Speckle Contrast Analysis (LSCA) technique extends the conventional laser speckle method to a nonscanning, full-field technique.

Needs exist for improved real-time measurement of blood perfusion and velocities. The needs are especially important in skin, skin flaps, surgical sites, transplants, breasts, and retinas. In the related art (U.S. Pat. No. 7,113,817), the system is started 60, aimed and focused 62, as shown in FIG. 1. The camera shutter exposure time, detector gain and aperture are separately set 64. A decision is made 66 to see if the target tissue is in the view finder. If the answer is no 68, a return to the aim and focus step 62 is required. If the answer is yes 70, the trigger shutter 72 is tripped, and the PC interrogates the detector to obtain a visual image 74. A decision is made 76 to see if the visual image contains the targeted tissue. If the answer is no 77, a return to step 62 is required. If the answer is yes 78, the system decides whether to obtain a laser speckle image 80. If a laser speckle image is not desired 82, the system is stopped 84.

If a laser speckle image is to be obtained 86, the laser is turned on 88, and the laser is aimed 90 at the target tissue. A laser filter 92 is inserted. The exposure time, detector gain and aperture are set 94, and the shutter is triggered 96. The detector is interrogated 98 to obtain a laser speckle image, and it is determined 100 if there are any saturated pixels. If saturated pixels exist 102, the system returns to adjust the exposure time, detector gain and/or aperture 94. If there are no saturated pixels 104, speckle contrast is computed 106 from the data obtained from the detector. The system uses multiple scattering corrections to obtain characteristic velocity 108. It maps the characteristic velocity onto the image of the tissue 112, displays the velocity mapping 110, and archives the data 114. An inquiry is made whether it is desired to obtain another image 116 of the same view from the same sample. If the answer is yes 118, the system returns to step 94 and sets the exposure time, detector gain and aperture for another image. If it is not desired to obtain another image 120, a decision is made 122 whether to obtain a different view. If the answer is yes 124, the system returns to the aim and focus step 62. If the answer is no 126, the system stops 84.

Although the related art system in U.S. Pat. No. 7,113,817 can use multiple scattering corrections to obtain characteristic velocity 108, the system in the related art does not use different images obtained at different exposure times of the same scene to create a combination image by dynamically correcting the geometric dependent parameter (the optical coherence parameter β) and/or the number of times a photon collides with red blood cells (m). This invention is an improvement upon the LSCA/MS technique described in U.S. Pat. No. 7,113,817, which is hereby incorporated by reference in its entirety. The present invention improves the accuracy of the blood velocity measurement using algorithms that compute blood velocity by selectively combining multiple images, thereby dynamically correcting the geometric dependent parameter (the optical coherence parameter β) and/or the number of times a photon collides with red blood cells (m) to obtain a more stable, reproducible, and accurate measurement of blood velocity.

SUMMARY OF THE INVENTION

Accordingly, the present invention is directed to multiple images, multiple exposure times, optical imaging of blood circulation velocities that substantially obviates one or more problems due to limitations and disadvantages of the related art.

An object of the present invention is to provide a blood velocity measurement by selectively combining multiple images of the same scene obtained by different exposure times.

Another object of the present invention is to provide an accurate blood velocity measurement using dynamic correction of the optical coherence (β) and the number of times a photon collides with red blood cells (m).

Another object of the present invention is to provide a more stable, reproducible, and accurate measurement of blood velocity.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, the method of measuring blood velocity includes obtaining a first velocity image by illuminating a tissue surface with a light source for a first exposure time, obtaining a second velocity image by illuminating the same scene of the same tissue surface with the same light source and the same illumination geometry for a second exposure time, computing a first average intensity of a first pixel block at a first predetermined location of the first velocity image and a second average intensity of the corresponding pixel block at the same predetermined location of the second velocity image, identifying mid-range velocities of the first and second pixel blocks, computing an optimal optical coherence parameter based on the mid-range velocity of the first pixel block and the mid-range velocity of the second pixel block, and iteratively re-computing the first velocity image and the second velocity image using the optimal optical coherence parameter.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE PREFERRED EMBODIMENTS

Reference will now be made in detail to the preferred embodiments of the present invention, examples of which are illustrated in the accompanying drawings.

This invention is an improvement on a method of optical imaging of blood circulation velocities using the laser speckle contrast and multiple scattering analysis method (LSCA/MS) described in U.S. Pat. No. 7,113,817, hereby incorporated by reference in its entirety. It utilizes multiple images at varying exposure times to obtain a quantitative measurement of blood circulation velocity.

Figure 1:
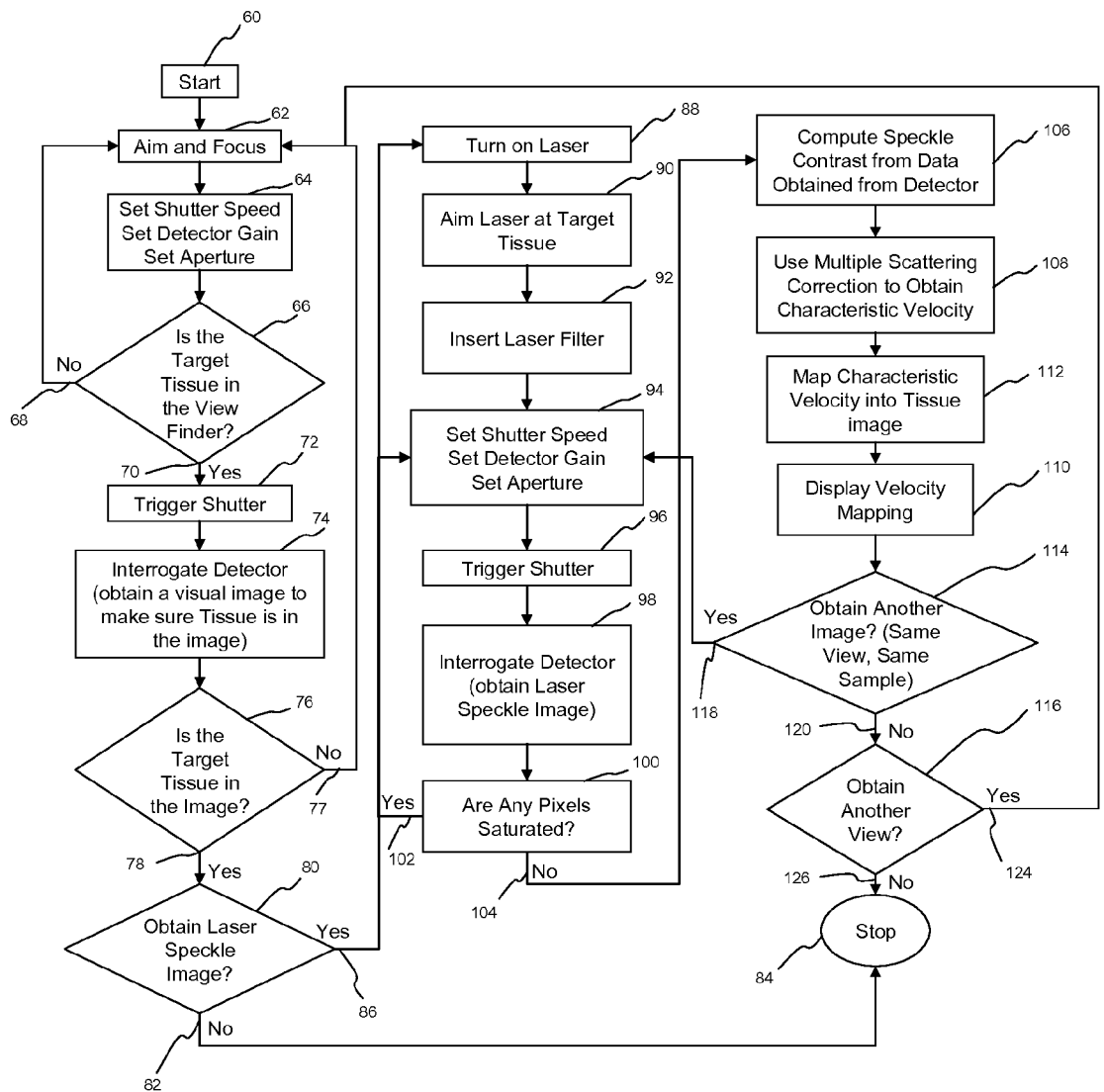
FIG. 1 is a schematic representation of steps for obtaining blood velocity values according to the related art.
Figure 2:
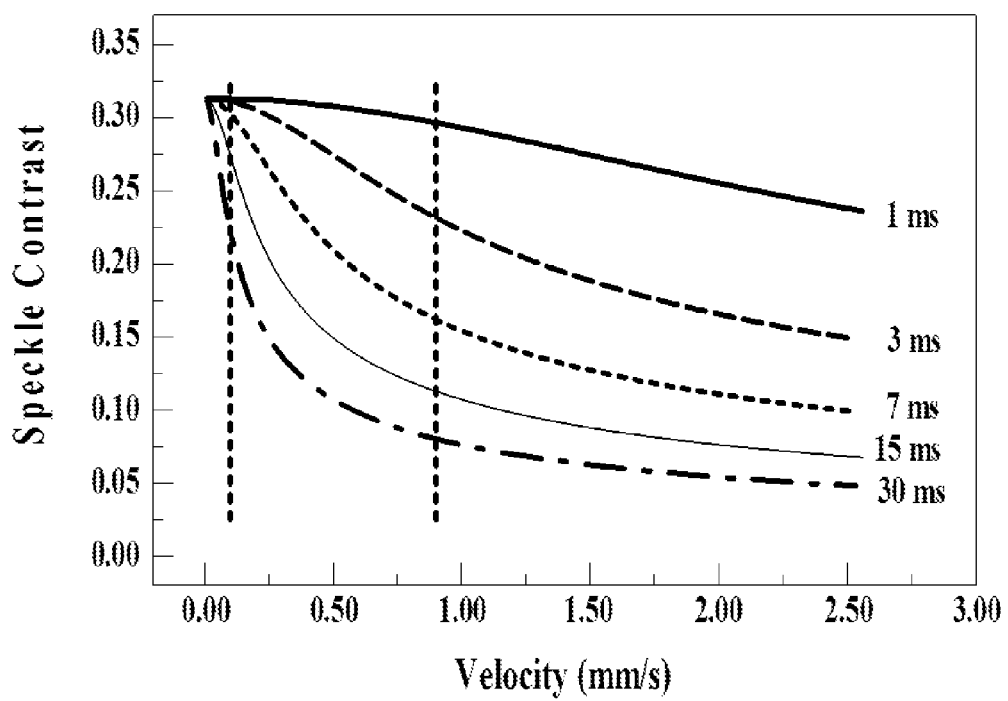
FIG. 2 is an exemplary graphical representation of the relationship between speckle contrast (d) and characteristic velocity ($V_c$) at five different exposure times (τ). The range of normal human capillary blood velocities is indicated by the dashed lines.

The accuracy of the blood velocity measurement is a function of the exposure time chosen. FIG. 2 shows an exemplary relationship between speckle contrast, characteristic velocity, and exposure time. The figure shows that a short exposure (1 ms-3 ms) is required for the retrieval of blood velocities faster than 0.7 mm/s and a long exposure (7 ms-15 ms) is required for the retrieval of slow velocities (<0.25 mm/s), since for data interpolation, a smooth, steep relation provides higher accuracy.

Figure 3:
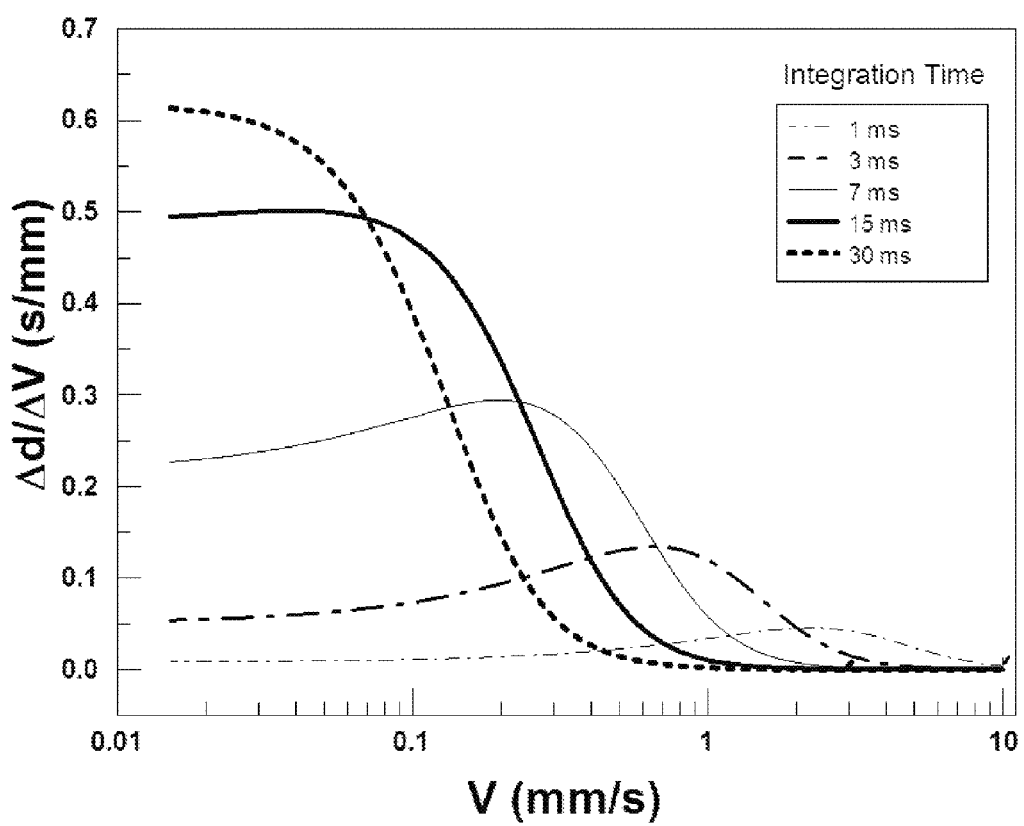
FIG. 3 is a graphical representation of ($\Delta d/\Delta V_c$) vs. $V_c$. Accuracy of the interpolation of $\Delta V_c$ from $\Delta d$ is maximized near the peak of the ($\Delta d/\Delta V_c$) vs. $V_c$ curve.

The relationship between speckle contrast, characteristic velocity, and exposure time can be seen more easily on a logarithmic scale. The most accurate reading for a given exposure time occurs when there is the greatest change in unit speckle contrast ($\Delta d$) per change in unit characteristic velocity ($\Delta V_c$). FIG. 3 shows the ($\Delta d/\Delta V_c$) vs. $V_c$ on a semilog scale. The peak of each exposure time curve corresponds to the most accurate blood velocity value.

Speckle contrast obtained from a single exposure time does not provide sufficient accuracy over a wide range (e.g., 0.05 mm/s to 5 mm/s) of characteristic blood velocities. Each exposure time is best suited for a certain range of velocities as described above. Longer exposures result in better accuracy for slower velocities and faster velocities are better determined with shorter exposure times. In U.S. Pat. No. 7,113,817, blood velocities are measured using a fixed and static optical coherence parameter (β) and the number of times a photon collides with red blood cells (m).

However, when a wide range of characteristic velocity is expected, accuracy of the measured blood velocity is degraded. The present invention takes multiple images of the same scene taken in rapid succession at two or more exposure times using new analytical techniques to dynamically compute highly accurate blood velocity values.

Two exemplary improvements of the present invention over U.S. Pat. No. 7,113,817 are (1) the use of different exposure times for images of the same scene taken in rapid succession and (2) new analytical techniques that exploit the new procedure to produce more accurate calculations of blood velocity using dynamically optimized, rather than fixed values of β and m. Blood velocity varies as a function of the size and elasticity of the vessel, and/or the time elapsed since the most recent heartbeat, but generally stays within a narrow range such that an educated guess of blood velocity can be made. Using that estimate, exposure times are chosen that bracket the expected velocity. For example, if the expected blood velocity is 0.5 mm/s, optimized exposure times are chosen for velocities in the vicinity of the expected velocity, such as 3 ms and 7 ms, as seen in FIG. 3 (0.5 mm/s is located around the mid-point of the 3 ms and 7 ms exposure time curves). An area is imaged, with data acquisition triggered by successive heartbeats in variable blood flow areas.

In data retrieval, there are two important parameters: optical coherence (β) and the number of times a photon collides with red blood cells (m). The data consist of multiple images of the same scene acquired at the same point in the cardiac cycle using multiple exposure times. These same-scene images are registered using landmarks. For example, in retinal images, the landmarks can be the optical nerve head, macula, and the retinal vasculature. Velocity is first computed for each exposure using the method described in U.S. Pat. No. 7,113,817. Pixels from all exposures with middle-range velocities are then found. Middle-range velocities are found by determining the range of velocities in the velocity images of the same scene, finding the center velocity value, and using the center velocity value ±20% as middle-range velocities. One of ordinary skill in the art would know that the range of center velocity can be improved to ±15%, ±10%, or other numbers. Depending on the range of blood velocities, a smaller or larger percentage can be used to define middle-range velocities. These middle-range velocities are assumed to be the same across all exposures. Middle-range velocity values found at the same pixel locations in all exposures are used to fit β and m using the singular value decomposition (SVD) or other multivariate methods. Velocities are re-computed with optimized values of β and m, using faster velocities from short exposure images and slower velocities from long exposure images. This process of fitting β and m, and calculating their optimized values can be done iteratively in order to further refine the accuracy of the final velocity values.

Mathematical Relations

Spatial distribution of the digitized image can be obtained by computing the average intensity <I(x, y)> over the square neighborhood of a point (x, y) of interest. One of ordinary skill in the art would know that although a square pixel box would be easier to implement, the pixel block can be any shape as long as the center point is (x, y). The speckle contrast d(x, y) is defined by:

$$d(x, y) = \frac{\sigma(x, y)}{\langle I(x, y) \rangle} \quad (1)$$

where σ(x, y) is the standard deviation of intensity over the square neighborhood. The intensity averaging process removes background contributions from surface roughness. Both d and σ depend on the statistics of blood velocity distribution and are affected by the presence of multiple scattering. Spatial properties of the time-averaged speckle pattern are equivalent to the temporal properties of the same pattern.

The variance $\sigma^2$ of the spatial intensity variations equals the time average of the autocovariance $C_V(t)$ of the intensity fluctuations, $$\sigma^2(T) = \frac{1}{T}\int_0^T C_V(\tau)d\tau \quad (2)$$
$$= \frac{1}{T}\int_0^T \langle [I(t) - \langle I \rangle][I(t+\tau) - \langle I \rangle]\rangle d\tau$$

where T is the integration time (i.e., exposure time).
For a stationary process, $C_V(\tau)$ can be written as:

$$C_V(\tau) = \langle I \rangle^2 C_t^2(\tau) \quad (3)$$

where $C_t(\tau)$ is the autocorrelation function. Using single scattering approximation, $C_t(\tau)$ is expressed as a smooth negative exponential function, $C_t(\tau) = \exp(-\tau/\tau_c)$ where $\tau_c$ is the correlation time. The speckle contrast d at any point (x, y) in a pattern integrated over time T is written as $$d(x, y) = \left[\frac{\tau_C}{2T}(1 - \exp(-2T/\tau_C))\right]^{1/2} \quad (4)$$

Assuming that the characteristic (i.e., average) velocity $V_c$ is related to $\tau_c$ ($V_c = \lambda(2\pi\tau_c)^{-1}$), where λ is the wavelength, Eq. (4) can be solved for $\tau_c$ using d and T. The value of $V_c$ can then be computed.

$$V_c = \int_0^\infty V g(V) dV \quad (5)$$

where g(V) is the assumed velocity distribution. The velocity distribution of RBCs can be described by Lorentzian, Maxwellian, Gaussian, or other distributions. The distribution of velocities leads to "Doppler-broadening" of the frequency distribution of the scattered light. In LDV, the frequency difference of the incident and scattered light is given by $\Delta f = v_l(f/c)$, where $v_l$ is the longitudinal component of the velocity, c is the speed of light, and f is the frequency of the incident radiation. Multiple scattering from flowing blood cells and stationary tissue complicates the procedure for retrieving blood velocity parameters from intensity fluctuations. Evolution of the phase difference of the scattered light can be treated as a series of scattering events. The Δf is a linear function of the particle velocity and has its origin in the Doppler effect. The mean Δf of photons emerging from tissue can be calculated by integrating the scattering intensity over all possible events. The expression for $C_t(\tau)$ can be written as:

$$C_t(\tau) = 1 + \beta(\exp(2m[I_i(\tau)-1]) - \exp(-2m)) \quad (6)$$

where β is the optical coherence of the signal at the viewing position, m is the average number of collisions the photon undergoes with a moving particle, and $I_i(\tau)$ is an intermediate scattering function defined by $$I_i(\tau) = \frac{\int_{-\pi}^{\pi} S(|Q(\theta)|)\langle\exp[iQ(\theta)\cdot\Delta R(\tau)]\rangle\sin(\theta)d\theta}{\int_{-\pi}^{\pi} S(|Q(\theta)|)\sin(\theta)d\theta} \quad (7)$$

where ΔR(τ) is the displacement of the center of mass of the moving particle during time τ, θ is the scattering angle, Q(θ) is the Bragg scattering vector, and S(Q(θ)) is the structure factor of the average scatterer. Q(θ) can be written as:

$$Q(\theta) = |Q(\theta)| = \frac{4\pi n}{\lambda}\sin\left(\frac{\theta}{2}\right) \quad (8)$$

where n is the refractive index of the moving particle at λ. S(Q(θ)) can be approximated using the Rayleigh-Gans theory, $$S(Q) = \left[\frac{3}{(Qa)^3}(\sin(Qa) - \cos(Qa))\right]^2 \quad (9)$$

where a is the effective radius (2.75 μm) of the RBC.

Figure 4:
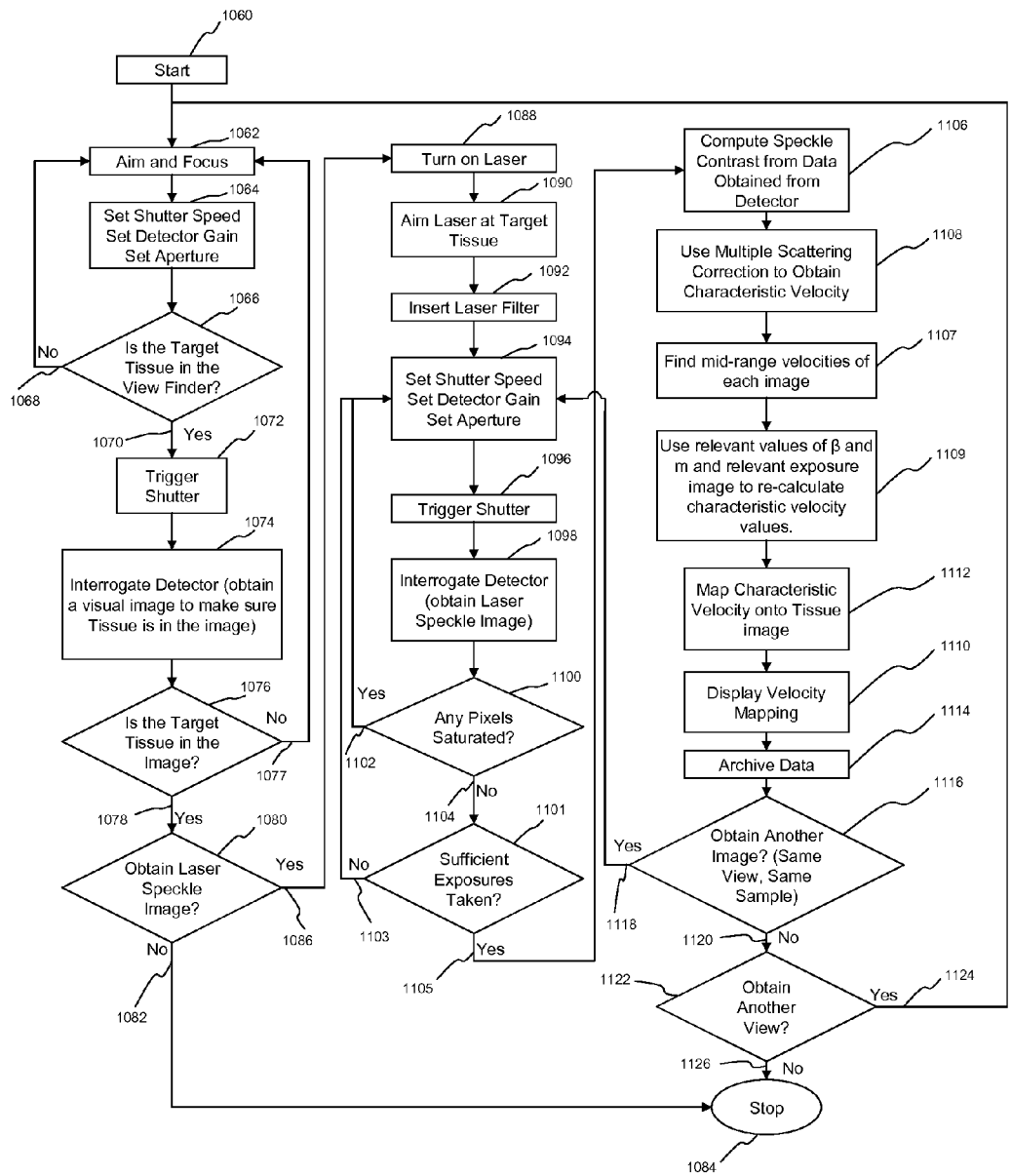
FIG. 4 is an exemplary schematic representation of steps for obtaining blood velocity values according to the present invention involving multiple laser speckle images at multiple exposure times.

The algorithm for data analysis in the current invention is significantly different from that in U.S. Pat. No. 7,113,817. For example, at least two images of the same scene are acquired at different exposures. In an exemplary embodiment shown in FIG. 4, the system is started 1060, aimed and focused 1062. The camera shutter exposure time, detector gain and aperture are separately set 1064. A decision is made 1066 to see if the target tissue is in the view finder. If the answer is no 1068, a return to the aim and focus step 1062 is required. If the answer is yes 1070, the shutter 1072 is triggered, and the PC interrogates the detector to obtain a visual image 1074. A decision is made 1076 to see if the visual image contains the targeted tissue. If the answer is no 1077, a return to step 1062 is required. If the answer is yes 1078, the system decides whether to obtain a laser speckle image 1080. If a laser speckle image is not desired 1082, the system is stopped 1084.

If a laser speckle image is to be obtained 1086, the laser is turned on 1088, and the laser is aimed 1090 at the target tissue. A laser filter 1092 is inserted. The exposure time, detector gain and aperture are set 1094, and the shutter is triggered 1096. The detector is interrogated 1098 to obtain a laser speckle image, and it is determined 1100 if there are any saturated pixels. If saturated pixels exist 102, the system returns to adjust the exposure time, detector gain and/or aperture 1094.

If there are no saturated pixels or the number of saturated pixels did not exceed a predetermined number (i.e., an arbitrary zero baseline) 1104, an inquiry is made as to whether sufficient exposures have been taken 1101. If the answer is no 1103, the system returns to step 1094 and sets the exposure time, detector gain and aperture for another image. If the answer is yes 1105, speckle contrast is computed 1106 from the data obtained from the detector. The system uses multiple scattering corrections to obtain characteristic velocity 1108. Before the characteristic velocity is mapped onto the image of the tissue 1112, mid-range velocities of each images are identified 1107, the optical coherence parameter (β) and the number of times a photon collides with red blood cells (m) are computed based on the identified mid-range velocities. Then, the characteristic velocity values are iteratively re-computed using the computed optical coherence parameter (β) and the number of times a photon collides with red blood cells (m) using each respective exposure time 1109.

Thereafter, the characteristic velocity map is displayed 1110 and the data are archived 1114. An inquiry is made whether it is desired to obtain another image 1116 of the same view from the same sample. If the answer is yes 1118, the system returns to step 1094 and sets the exposure time, detector gain and aperture for another image. If it is not desired to obtain another image 1120, a decision is made 1122 whether to obtain a different view of the same sample. If the answer is yes 1124, the system returns to the aim and focus step 1062. If the answer is no 1126, the system stops 1084.

Unlike the method in U.S. Pat. No. 7,113,817, where images of the same scene of the same sample taken with multiple, different exposures are analyzed independently without a dynamic correction of the optical coherence parameter (β) and/or the number of times a photon collides with red blood cells (m), whereas in this invention, these images are analyzed at the same time. In areas of the body where flow is not constant and depends on the state of the cardiac cycle, the image acquisition is triggered by the same point in the cardiac cycle, therefore each image is taken during a successive heartbeat. In areas where blood flow is more constant, more rapid image acquisition can take place without the aid of the cardiac trigger.

A detailed exemplary embodiment of steps 1107 and 1109 will be further described. After at least two images are taken at different exposure times of the same scene, the additional steps in the algorithm are as follows:

(1) Compile a look-up table relating the possible values of d (speckle contrast) and $V_C$ (blood velocity) for a given observational geometry and exposure. The d values range from 0 to 1. The program allows input of a variable increment of d, such as 0.002. $V_C$ is then computed for each d, using typical values of β (e.g., 0.5) and m (e.g., 1.7).

(2) Compute the average intensity, <I(x, y)>, for each pixel block, assign this value to the central pixel of the block, and repeat the computation process for every pixel in the image. Identify the mid-range velocity at pixel (x, y) from at least two different-exposure images of the same scene and compute its value. The mid-range velocities from different exposures are assumed to be the same. The SVD method or other multivariate methods can be used to compute optimal values of β and m.

(3) Compute the variance ($\sigma^2$) and standard deviation of intensity (σ) for each pixel block according to Eq. 2.

(4) Calculate d(x, y) for each pixel according to Eq. 1.

(5) Interpolate the $V_C$ value using the look-up table and apply a constant multiplier to d, such as 1024, to convert its value to an integer so that it can be stored in an electronic image format such as BMP.

(6) The optimal values of β and m calculated in step (2) are then used to re-compute $V_C$ for each of the multiple-exposure-time velocity images according to Eq. 5 using each respective exposure time. For example, a shorter exposure is used for faster velocities.

(7) Steps (2)-(6) are performed reiteratively with output values from step (6) as input values in the next iteration in order to produce more accurate velocity calculations.

(8) Velocities obtained from fitted values of β and m are mapped onto one digital image. Fast velocities are used from short exposure images, whereas slow velocities are used from long exposure images.

It will be apparent to those skilled in the art that various modifications and variations can be made in the multiple images, multiple exposure times, optical imaging of blood circulation velocities of the present invention without departing from the spirit or scope of the invention. According to one exemplary embodiment of the present invention, simplified numbers can be superimposed on the images of the blood velocity map to help surgeons read the blood velocity map while he is performing an operation. For example, the number 1 can be used to represent that the blood velocity in a first region is identical to average, normal blood velocities of the first region. In addition, the number 1.2 can be used in a second region of the same image to help the surgeon recognize that the blood velocity at the second region is 20% faster than that of the average, normal blood velocity of the first region. Alternatively, numbers can be used to represent the average blood velocity of a selected region, and/or the average blood velocity of the entire image.

According to another exemplary embodiment of the present invention, color coding can be superimposed as background colors on the images of the blood velocity map to help surgeons read the blood velocity map while he is performing an operation. For example, color coding can be used to show the differences between regions with average, normal blood velocities, regions with wounds, and regions with vascular compromise. Thus, it is intended that the present invention cover the modifications and variations of this invention provided they come within the scope of the appended claims and their equivalents.

What is claimed is:

1. A method of measuring blood velocity, comprising the steps of:
    obtaining a first velocity image from multipoint dynamic scattering by illuminating a selected tissue surface for a first exposure time at a selected cardiac cycle point of a first cardiac cycle;
    obtaining a second velocity image from multipoint dynamic scattering by illuminating the selected tissue surface for a second exposure time at the selected cardiac cycle point of a second cardiac cycle;
    computing a first average intensity of a first pixel block at a first predetermined location of the first velocity image and a second average intensity of a second pixel block at a second predetermined location of the second velocity image;
    identifying mid-range velocities of the first and second pixel blocks;
    computing an optimal optical coherence parameter based on the mid-range velocity of the first pixel block and the mid-range velocity of the second pixel block; and
    iteratively re-computing the first velocity image and the second velocity image using the optimal optical coherence parameter.

2. The method of claim 1, further comprising:
    computing an optimal number of times a photon collides with red blood cells based on the mid-range velocity of the first pixel block and the mid-range velocity of the second pixel block; and
    iteratively re-computing the first velocity image and the second velocity image using the optimal number of times a photon collides with red blood cells.

3. The method of claim 2, wherein a multivariate method is used in computing the optimal number of times a photon collides with red blood cells based on the mid-range velocity of the first pixel block and the mid-range velocity of the second pixel block.

4. The method of claim 1, further comprising computing a third velocity image using portions of the first velocity image and portions of the second velocity image.

5. The method of claim 4,
    wherein a portion of the first velocity image having a first predetermined velocity is used to compute the third velocity image, and
    wherein a portion of the second velocity image having a second predetermined velocity is used to compute the third velocity image,
    provided the first exposure time is shorter than the second exposure time, and the first predetermined velocity is faster than the second predetermined velocity.

6. The method of claim 4, wherein the third velocity image is converted into a form that is capable of being stored in an electronic image format.

7. The method of claim 1, wherein the first pixel block at the first predetermined location of the first velocity image and the second pixel block at the second predetermined location of the second velocity image map a same location of a same scene.

8. The method of claim 1, wherein a multivariate method is used in computing the optimal optical coherence parameter based on the mid-range velocity of the first pixel block and the mid-range velocity of the second pixel block.

9. The method of claim 1, wherein the mid-range velocity of the first pixel block is determined to include a center velocity value among ranges of velocities during the first exposure time.

10. The method of claim 1, wherein the mid-range velocity of the second pixel block is determined to include a center velocity value among ranges of velocities during the second exposure time.

11. The method of claim 10, wherein the mid-range velocity of the second pixel block is determined to further include a range within ±20% of the center velocity value.

12. The method of claim 10, wherein the mid-range velocity of the second pixel block is determined to further include a range within ±15% of the center velocity value.

13. The method of claim 10, wherein the mid-range velocity of the second pixel block is determined to further include a range within ±10% of the center velocity value.

14. The method of claim 1, further comprising designating numbers to regions of a blood velocity map obtained by the iterative re-computing, wherein the numbers represent blood velocities of corresponding regions.

15. The method of claim 1, further comprising designating background colors to regions of a blood velocity map obtained by the iterative re-computing, wherein the background colors represent blood velocities of corresponding regions.

* * * * *